United States Patent [19]
Cini et al.

[11] Patent Number: 5,705,485
[45] Date of Patent: *Jan. 6, 1998

[54] GEL FORMULATIONS CONTAINING GROWTH FACTORS

[75] Inventors: John Cini, Gilford, Conn.; Amy Finkenaur, Neshanic Station, N.J.

[73] Assignee: Ethicon, Inc., Somerville, N.J.

[*] Notice: The term of this patent shall not extend beyond the expiration date of Pat. No. 5,457,093.

[21] Appl. No.: 539,898

[22] Filed: Oct. 6, 1995

Related U.S. Application Data

[63] Continuation-in-part of Ser. No. 520,798, Aug. 30, 1995, which is a continuation of Ser. No. 135,230, Oct. 12, 1993, Pat. No. 5,457,093, which is a continuation-in-part of Ser. No. 974,013, Nov. 10, 1992, Pat. No. 5,427,778, which is a continuation of Ser. No. 703,584, May 20, 1991, abandoned, which is a continuation of Ser. No. 233,483, Aug. 19, 1988, abandoned, which is a continuation-in-part of Ser. No. 98,816, Sep. 18, 1987, abandoned.

[51] Int. Cl.$^6$ .................. A61K 38/00; C07K 14/00; C07K 1/00; C07K 17/00
[52] U.S. Cl. .................. 514/12; 514/21; 530/399; 424/78.08; 424/94.1
[58] Field of Search .................. 514/12, 21; 530/399; 424/78.08, 94.1

[56] References Cited

U.S. PATENT DOCUMENTS

| | | | |
|---|---|---|---|
| 4,717,717 | 1/1988 | Finkenaur | 514/12 |
| 5,124,316 | 6/1992 | Antoniades et al. | 514/12 |
| 5,457,093 | 10/1995 | Cini et al. | 514/12 |

OTHER PUBLICATIONS

Johnsson et al. The EMBO Journal 3(5), 921–928, (1984).
"Hydrogels in Medicine and Pharmacy", vol. 2, in Polymers, ed. N. Peppas, pp. 116–124 (1987).

*Primary Examiner*—Cecilia J. Tsang
*Assistant Examiner*—P. Lynn Touzeau
*Attorney, Agent, or Firm*—John W. Wallen, III

[57] ABSTRACT

Gel formulations containing polypeptide growth factors having human mitogenic or angiogenic activity are provided. The gel formulations are useful for topical or incisional wound healing for cutaneous wounds, particularly in the anterior chamber of the eye. The gel formulations also comprise a water soluble, pharmaceutically or ophthalmically compatible polymeric material for providing viscosity within various ranges determined by the application of the gel. The gel formulations provide controlled release and increased contact time of the growth factor to the wound site.

36 Claims, No Drawings

GEL FORMULATIONS CONTAINING GROWTH FACTORS

BACKGROUND OF THE INVENTION

This application is a continuation-in-part of U.S. Ser. No. 520,798, filed Aug. 30, 1995, which is a continuation of U.S. Ser. No. 135,230, filed Oct. 12, 1993, now U.S. Pat. No. 5,457,093, which is a continuation-in-part of U.S. Ser. No. 974,013, filed Nov. 10, 1992, now U.S. Pat. No. 5,427,778, which is a continuation of U.S. Ser. No. 703,584, filed May 20, 1991, now abandoned, which is a continuation of U.S. Ser. No. 233,483, filed Aug. 19, 1988, now abandoned, which is a continuation-in-part of U.S. Ser. No. 098,816, filed Sep. 18, 1987, now abandoned.

Throughout this disclosure, various publications, patents and patent applications are referenced. The disclosures of these publications, patents and applications in their entireties are hereby incorporated by reference into this disclosure in order to more fully describe the state of the art as known to those skilled therein as of the date of the invention described and claimed herein.

The present invention relates to gel formulations containing polypeptide growth factors having human mitogenic or angiogenic activity.

The human polypeptide growth factors are molecules that regulate the growth of normal human cells. Many human polypeptide growth factors have been identified and their chemical structures determined. Those falling within this group are: epidermal growth factor (EGF), acidic and basic fibroblast growth factor (FGF), platelet derived growth factor (PDGF), transforming growth factor-alpha (TGF-alpha), transforming growth factor-beta (TGF-beta), insulin-like growth factors (IGF-I and IGF-II), and nerve growth factor (NGF). Because of their ability to stimulate cell growth, the human polypeptide growth factors have been described as being useful in stimulating the wound healing process.

Heretofore, there has not been provided a suitable delivery system for any growth factor, for use in treating wounds. In particular, it is desirable to have a delivery system that controls the release of the growth factor to the wound and adheres to or maintains itself on the wound for an extended period of time in order to increase the contact time of the growth factor to the wound. The present invention provides such delivery systems in the form of gels containing growth factors. Biocompatible gel materials may be used to deliver a growth factor to a wound and provide the advantages of a controlled profile of delivery and a moist environment for the wound.

SUMMARY OF THE INVENTION

The present invention provides aqueous gel formulations or viscous solutions for the controlled delivery of growth factors to a wound site. The exact formulation employed will depend on the type of application that is desired. Three different applications are intended, namely gels for topical or incisional wound healing, gels for healing wounds in the anterior chamber of the eye and low viscosity, aqueous formulations for those applications requiring a more fluid formulation having a higher water content.

An aqueous gel formulation for topical or incisional wound healing comprises an effective wound healing amount of a polypeptide growth factor having human mitogenic or angiogenic activity. Additionally, this formulation contains a water soluble, pharmaceutically acceptable polymeric material for providing viscosity within the range 1,000 to 12,000,000 cps. Viscosity measurements are generally measured at either room temperature or at elevated temperatures. An aqueous gel formulation for use in healing wounds in the anterior chamber of the eye comprises a water soluble ophthalmically compatible polymeric material for providing viscosity within the range 1000 to 100,000 cps at room temperature. A low viscosity, aqueous formulation comprises a water soluble, pharmaceutically or ophthalmically compatible polymeric material for providing viscosity within the range 1 to 5,000 cps at room temperature. A preferred use for the low viscosity formulation is for ophthalmic wound healing. However, it may also be used for other types of wound healing, especially when used to soak a bandage placed on the wound.

The gel formulations of the present invention have the advantage of adhering to a wound and conforming to irregular body or wound contours. The gels may be applied directly to a wound site or in conjunction with a compliant porous or microporous substrate, for example in the form of a coating, to be applied to the wound site. Gels have the further advantages of having a high water content (which keeps the wound moist), the ability to absorb wound exudate, easy application to a wound and easy removal by washing. Gels have a cool feeling when applied to a wound and thus can increase patient comfort and acceptance of the formulation, especially on sensitive wounds.

The gel formulations of the present invention also provide a controlled delivery system for growth factors on a wound site. Controlled delivery refers to drug release sufficient to maintain a therapeutic level over an extended period of time up to 24 hours or more. Increased contact time of growth factors at the wound site has been reported to be necessary to achieve a significant increase in the rate of wound healing. The present gel formulations increase the contact time of the growth factor at the wound site and provide a sustained release dosage form. This is an important advantage because it permits less frequent application of the formulation to the wound and thereby permits less disturbance of the wound and its cellular components, particularly at the different phases of mitosis.

DETAILED DESCRIPTION OF THE INVENTION

The aqueous gels of the present invention can have different viscosities depending on the intended application of the gel. Viscosity is a measure of the resistance of a liquid to flow. It is defined as the ratio of the shearing stress to the rate of shearing. The shear stress is the resistance of the liquid to flow under the influence of an applied force, i.e., the molecular resistance within a body opposing an external force. The shear stress is defined as the ratio of the force to the area sheared. When a liquid is sheared, assuming laminar flow, the layers of the liquid move at different rates. The relative rate of motion of the layers is only one factor in the rate of shear. The other is the distance, or clearance between the shearing planes. Thus, shear rate is defined as the ratio of the velocity of the gel to the clearance. Viscosity has the dimensions of dynes/sec per cm2. These dimensions are referred to as poise. The dimensions of viscosity referred to herein, unless otherwise indicated, are in centipoise (cps) as measured using a Brookfield viscometer. All viscosity values are at room temperature, e.g. 22°–25° C., unless otherwise indicated.

The polypeptide growth factors referred to herein are those having human mitogenic or angiogenic activity selected from the group consisting of EGF, acidic FGF, basic-FGF, PDGF, TGF-alpha, TGF-beta, angiogenin, NGF, IGF-I, IGF-II or mixtures thereof. It is contemplated that biologically active fragments or chemically synthesized derivatives of these growth factors may be used instead of the entire naturally occurring molecule. In addition to mitogenic activity, EGF, the FGF's, the TGF's and angiogenin are reported to have angiogenic activity. It is preferred that the growth factor be prepared by recombinant DNA techniques.

As used herein, human EGF refers to EGF having that polypeptide sequence or any substantial portion thereof set forth in Urdea, M. S. et al., Proc. Natl. Acad. Sci. (USA) 80:7461–7465 (1983). Human EGF also refers to any naturally occurring human EGF variant such as gamma-urogastrone. Epidermal growth factor, human epidermal growth factor and the other growth factors may be isolated from natural sources, produced using recombinant DNA techniques or prepared by chemical synthesis.

As used in this application, EGF is intended to include the class of polypeptides that have biological activity similar to that exhibited by the natural human EGF polypeptide as measured in recognized bioassays, such as the EGF receptor binding assay described in U.S. Pat. No. 4,717,717, and which have certain conserved amino acid residues and common positioning of disulfide bonds, as discussed by Carpenter et al. in "Epidermal Growth Factor, its receptor, and related proteins", Experimental Cell Research, 164:1–10 (1986). Thus, EGF includes the EGF produced by recombinant DNA techniques, mouse EGF isolated from the submaxillary glands of mice, rat EGF, and natural human epidermal growth factor, which may be isolated from human urine, and bioactive derivatives and related polypeptides of any of the foregoing, including precursors that are transformed into active epidermal growth factor in situ by proteolytic processing.

PDGF is a major mitogen in serum which promotes the proliferation of mesenchymally-derived cells, such as fibroblasts, glial cells, and smooth muscle cells in vitro. Amino acid sequence data have demonstrated that PDGF is composed of two distinct, but homologous, polypeptide chains, namely the A-chain and the B-chain. These two chains have been found as dimers of PDGF-AA, PDGF-B and PDGF-AB. The amino acid sequences for the A and B chains of PDGF have been determined and that of the B chain is set forth in Johnsson, A. et al., 1984, EMBO J., 3:921–928. As used herein, the phrase "rhPDGF-B" shall mean the human B—B homodimer of PDGF produced by recombinant DNA techniques.

An effective wound healing amount of a polypeptide growth factor for use in the present invention may be within the range of about 0.01 to about 1,000 micrograms/ml. It is preferred that the growth factor concentration be about 1–500 micrograms/ml and more preferably 1–100 micrograms/ml. The gels of the present invention are capable of sustaining the release of the polypeptide growth factor.

The gel forming materials of the present invention may be water soluble polymers capable of forming a viscous aqueous solution or non-water soluble, water swellable polymers (e.g. collagen), which can also form a viscous solution. Swellable polymers are those which absorb water rather than dissolve in water. Cross-linked forms of the polymers described herein may not be water soluble but may be water swellable. Therefore, cross-linked forms of the polymers are within the scope of the present invention. Cross-linking refers to covalently bonding polymer chains together with a bifunctional reagent such as glutaraldehyde. Also, it is understood by those skilled in the art that certain polymers may have to be used in the salt form or partially neutralized in order to be made water soluble. For example, hyaluronic acid is preferred to be used as sodium hyaluronate to provide suitable water solubility.

In the aqueous gel formulations for topical or incisional wound healing, the polymer may be selected from the group consisting of vinyl polymers, polyoxyethylene-polyoxypropylene copolymers, polysaccharides, proteins, poly(ethylene oxide), acrylamide polymers and derivatives or salts thereof. It is understood that poly(ethyleneoxide) includes polyethylene glycol. In the gel formulations for use in healing wounds in the anterior chamber of the eye, the polymers may be the same except that it is not preferred to use the polyoxyethylene-polyoxypropylene copolymers or poly(ethylene oxide). Also, for anterior chamber use, it is preferred that the polymer be biodegradable, i.e. capable of breaking down into harmless constituents that can be drained from or metabolized in the anterior chamber. In the low viscosity, aqueous formulations for use in ophthalmic wound healing, the gel forming polymers may be the same as for topical or incisional wound healing, except that poly(ethylene oxide) is not preferred to be used.

The vinyl polymers (also known as substituted polyethylenes) useful in the present invention may be selected from the group consisting of polyacrylic acid, polymethacrylic acid, polyvinyl pyrrolidone and polyvinyl alcohol. The polysaccharides useful in the present invention may be selected from the group consisting of cellulose or cellulose derivatives, glycosaminoglycans, agar, pectin, alginic acid, dextran, starch, and chitosan. The more water soluble ∝-amylose is preferred. The glycosaminoglycans may be selected from the group consisting of hyaluronic acid, chondroitin, chondroitin-4-sulfate, chondroitin-6-sulfate, dermatan sulfate, keratan sulfate, heparin sulfate and heparin. The glycosaminoglycans may be used to enhance wound healing in combination with any other gel forming polymer. The proteins useful in the present invention may be selected from the group consisting of collagen, gelatin and fibronectin. The acrylamide polymers may be polyacrylamide or polymethacrylamide polymers. Biocompatible polyacrylamide polymers are preferred.

In the gel formulation for topical or incisional wound healing, the viscosity may be within the range 1,000–12,000,000 cps at room temperature. A preferred viscosity range is 1000–2,000,000. A still more preferred viscosity range is 1000–500,000 cps. The most preferred viscosity is 1000–150,000 cps. In one embodiment of the present invention, the topical gel formulation may comprise 0.1–5% by weight carboxymethylcellulose (CMC) or sodium carboxymethylcellulose (NaCMC) having a molecular weight of about 450,000–4,000,000. In a preferred embodiment, the CMC is present at 1.5–4% by weight and has a molecular weight of 450,000–4,000,000. The pH of the CMC gel should be within the range 4.5–8 and more preferably in the range 5–7.

In another embodiment, the topical and incisional gel of the present invention may comprise 15–60% by weight of a polyoxyethylene-polyoxypropylene block copolymer having an average molecular weight of about 500–50,000. In a preferred embodiment, the block copolymer is present at 15–40% by weight and has a molecular weight in the range 1,000–15,000. The block copolymers used in the present invention are commonly known as Pluronics. Preferred Pluronics are Pluronic F88 and F127.

In a further embodiment, the topical and incisional gel may comprise 0.5–10% by weight of hyaluronic acid having a molecular weight in the range 500,000 to 8,000,000. In a preferred embodiment, the hyaluronic acid is present at 1.5–6.0% by weight and the molecular weight is greater than 1,000,000.

Acrylamide polymers may be useful for all types of wound healing, particularly in the anterior chamber of the eye. An absorbable acrylamide polymer, such as polyacrylamide, may be a good substitute for present carrier systems used in ophthalmic applications, such as hyaluronic acid. The acrylamide polymers may have a molecular weight in the range 1–13 million, preferably about 4–6 million. The weight percent of the acrylamide polymer in the gel may be 2–5%, preferably 3.5–4.5%. Substituted acrylamide polymers, such as methyl and alkyl substituted polymers are also within the scope of the present invention.

For use in the anterior chamber of the eye, an acrylamide gel delivery system has the following characteristics: any products of the dissolution or degradation of the delivery matrix are nontoxic and do not clog the trabecular mesh work; the gel is optically transparent; and the gel can be left in the anterior chamber without causing adverse clinical effects such as an unacceptable increase in ocular pressure.

It will be readily apparent to one skilled in the art that the desired viscosity range may be achieved by varying the molecular weight and percent concentration of the polymer in the formulation. For example, a gel having a low viscosity may be achieved by using a low molecular weight polymer or a lower percent concentration or a combination of the two. A high viscosity gel may be achieved by using a higher molecular weight polymer and a higher percent concentration. Intermediate viscosities may be achieved by varying the molecular weight and percent concentration accordingly.

In those gel formulations requiring lower viscosities than the topical and incisional gel, namely the formulation for use in healing wounds in the anterior chamber of the eye and the low viscosity solution for ophthalmic wound healing, the percent concentration of the polymer and its molecular weight may be varied to achieve the desired viscosity. For instance, in anterior chamber use, the gel may comprise a cellulose polymer that is 1–20% by weight and has a molecular weight in the range 80,000 to 240,000. The preferred range of concentration is 1–3%. In another embodiment for anterior chamber use the gel may comprise hyaluronic acid at a concentration of 0.5–5% by weight and a molecular weight of 500,000–8,000,000. It is preferred that the hyaluronic acid be present at a concentration of 0.5%–2.0% and the molecular weight be 2,000,000–4,000,000. The preferred viscosity range for anterior chamber use is 1000–100,000 cps.

The low viscosity solution may comprise 0.1–2.0% by weight polyacrylic acid having a molecular weight of about 100,000–4,000,000. In a preferred embodiment, the polymer is present at 0.05–0.5%. In another embodiment, this dilute viscous solution may comprise 2–40% by weight of a polyoxyethylene-polyoxypropylene copolymer having an average molecular weight of 500–500,000. Preferably, the concentration is 2–20% and the molecular weight is 1,000–15,000. Alternatively, the dilute viscous solution may comprise a cellulose polymer at 1–20% and having a molecular weight of about 80–240,000. It is preferred that the concentration be in the range of 1–10%. In a further embodiment, the dilute viscous solution may comprise 0.5–5.0% by weight hyaluronic acid having a molecular weight of about 500,000–8,000,000. Preferably, the concentration is 0.5–2.0% and the molecular weight is 1,000,000–6,000,000. If the dilute viscous solution is to be used as eye drops, it is preferred that the viscosity be in the range 1–1000 cps. If it is used for other applications, such as soaking a bandage, then any viscosity in the range 1.0–5,000 will be suitable.

The cellulose polymers used in the gels of the present invention are capable of stabilizing the polypeptide growth factors against loss of biological activity in an aqueous solution. Use of cellulose polymers to stabilize EGF against loss of biological activity is described in U.S. Pat. No. 4,717,717. The cellulose polymers that are used in the present invention are water-soluble etherified cellulose polymers such as alkyl celluloses, hydroxyalkyl celluloses and alkylhydroxyalkyl celluloses, for example methyl cellulose, hydroxyethyl cellulose, carboxymethyl cellulose, hydroxypropylmethyl cellulose and hydroxypropyl cellulose. Methyl cellulose and the hydroxyalkyl cellulose derivatives such as carboxymethyl cellulose, hydroxypropyl cellulose, hydroxyethyl cellulose and hydroxypropylmethyl cellulose are preferred.

The stability of a PDGF cellulose polymer gel formulation can be greatly increased by including in the formulation a charged chemical species, such as a charged amino acid or a metal ion. Suitable amino acids which can be employed include lysine, arginine, histidine, aspartic acid, glutamic acid, alanine, methionine, proline, serine, asparagine and cysteine. Aminoguanidine and protamine may also be employed. Suitable metal ions which can be employed in the gel formulation include zinc and magnesium. The amino acid may be employed as the free acid or as a salt such as the hydrochloride salt. As used herein, "stability" refers to a prevention of the loss of mitogenic activity of the PDGF in the gel or an increase in the amount of PDGF protein that is released from the gel. As such the present invention provides PDGF gel formulations that are useful for treating wounds.

The increase of PDGF stability in a CMC gel can be accomplished by minimizing the charge interactions between PDGF or by mimimizing interaction with the reducing ends of the CMC by adding competing positively or negatively charged counterions. It is advantageous to add a preservative to the formulation during preparation or to sterilize the formulation by, for example, filtration or the application of heat at a temperature of about 122° C. for several minutes under pressure up to about 1 bar.

The gel formulations of the present invention may be used to coat fibers of an absorbent gauze dressing to form a wound healing bandage which may then be placed on a wound. The low viscosity formulation is preferred for this use. The wound healing bandage may be prepared by soaking a gauze dressing with an aqueous gel solution containing a human polypeptide growth factor having mitogenic activity. The bandage can then be applied to the wound so that the coated fibers of the gauze contact the wound and stimulate cell growth to increase the rate of wound healing.

The gels of the present invention are useful in eye drop formulations, ophthalmic irrigating solutions, salves for wound healing and the like. Wounds that may be healed using the compositions of the present invention are those which result from any accidental or medical injury which causes epithelial damage such as ophthalmic wounds, which result from corneal ulcers, radiokeratotomy, corneal transplants, epikeratophakia and other surgically induced wounds in the eye; and cutaneous wounds such as burn wounds, incisional wounds, donor site wounds from skin transplants, and ulcers (cutaneous, decubitis, venous stasis and diabetic). As used herein, ophthalmic wound healing includes anterior chamber wound healing as well as subconjunctival wound healing. The gels of the present invention may also be used for healing internal incisions as well as internal wounds such as gastric ulcers.

In those applications where the gel is applied to an internal or incisional wound, it is preferred that the gel forming polymer be degradable. The naturally occurring polymers are generally degradable. Examples of these are collagen, the glycosaminoglycans, gelatin and starch. The cellulosics are not degradable. The synthetic polymers such as the vinyl polymers are not degradable. The biodegradability of the polymers described herein is well known to those skilled in the art.

The following examples are presented to illustrate the subject invention. The invention is not to be considered limited by these examples, but only by the appended claims.

EXAMPLE 1

Carboxymethylcellulose Gels

Carboxymethylcellulose (CMC or NaCMC) gels were prepared according to the present invention. Preferred grades of sodium carboxymethylcellulose are those referred to as pharmaceutical grade CMC (NaCMC) 7H3SFPH. The following ingredients were added to 226.2 kg of water for injection (WFI) at 80° C.: 1946.3 g of sodium chloride and 1203.5 g of L-lysine hydrochloride in a 350 L Fryma mixing vessel. The mixture was stirred for 10 minutes. With an internal homogenizer turned on (approximately 2850 rpm), 5776.8 g of NaCMC was added in less than 5 minutes. The homogenizer was turned off after 10 minutes. The mixture was stirred at 44 rpm and cooled to 25° C. When the temperature reached 25° C., the mixture was evacuated to −0.8 bar. The mixture was then sterilized at 122° C. for 20 minutes.

After the sterilization, the mixture was cooled to 25° C. and the following ingredients were mixed together: 11.712 L WFI, 377.9 g of sodium acetate trihydrate and 15.6 g of acetic acid. These ingredients were added aseptically into the gel by filtering through a sterilizing filter. The mixture was stirred for 30 minutes. A solution of rhPDGF-B (25 g) in 2500 mL WFI was aseptically added to the gel, by filtration, with mixing. This was followed by a 250 mL WFI rinse. The gel was mixed for 2 hours and then aseptically transferred to a stainless steel transportation vessel. The gel was transferred to a filling facility and filled into form-fill-seal containers. The gel had a viscosity of 2883 cps measured at 37° C.

EXAMPLE 2

Carboxymethylcellulose Gels

Carboxymethylcellulose gels were prepared according to the following procedure:

To 1900 g of high purity water heated to 70°–80° C. was added 3.24 g of methylparaben, and 0.36 g of propylparaben and stirred until dissolved by visual examination. After the parabens were dissolved, 3.14 g of sodium acetate and 8.086 g of sodium chloride was added and the heat source removed. After the chemicals were dissolved, the solution was cooled to 15°–30° C. To the cooled solution was added 136 ul of acetic acid and 1.74 ml of m-cresol. After sufficient mixing, the pH of the buffer was measured (pH=5.63)and the buffer was brought to a final volume (~2 L) with water. The final pH of the buffer was 5.60. To 585.6 g of the buffer solution in a 1 L polycarbonate bottle was added 3.0 g of L-lysine monohydrochloride and the mixture was stirred until visually dissolved. Using a Lightning Labmaster mixer set at 1300 RPM, 14.4 g of Aqualon CMC, grade 7H3SFPH, was added within 30 sec. to the buffer solution using a modified funnel and the gel was mixed for a total of 90 min. to yield a 2.4% CMC gel.

The gel was formulated at 100 ug/g rhPDGF-B/gm of gel based on mass as calculated using optical density (OD @280 nm) of rhPDGF-B drug substance solution as follows: To the 2.4% CMC gel was added 6 g of rhPDGF-B drug substance (OD=10.0 mg/ml) using a syringe and injecting the drug substance into the gel at several locations. The gel was hand mixed for a few minutes and mixed with a Heidolph mixer at 300 RPM for 1 hr. under 0.2 um-filtered nitrogen. The gel was then rolled on a roller mill for 1 hr. at low speed. The rhPDGF-B/CMC gel was then packaged in 15-g capacity Teledyne laminate tubes (~10 g/tube) and the tubes sealed with a Kalix heat sealer. Total yield was 55 tubes.

EXAMPLE 3

Carboxymethylcellulose Gels

Carboxymethylcellulose (CMC or NaCMC) gels were prepared according to the present invention. Preferred grades of sodium carboxymethylcellulose are those referred to as pharmaceutical CMC (NaCMC) 7H3SFPH. 48.6 g of Methylparaben and 5.4 g of propylparaben was added to 28.4 kg of water in a 50 L Fryma mixing vessel and heated to 80° C. and maintained for 1 hr. The mixture was cooled to 30° C. and with the anchor motor at 16 rpm, the following excipients were added: 47.1 g of sodium acetate, 242.6 g of sodium chloride and 150 g of l-lysine hydrochloride and 2.0 g of glacial acetic acid. With the anchor motor off and the dissolver disk set beween 1300 and 1600 rpm, 720 g of CMC powder was added in less than 1 minute into the liquid vortex. After CMC was added, the anchor motor was turned on and the resultant mixture was mixed for one hour. The dissolver disk was turned off after 6 minutes.

After one hour mixing, the mixture was sterilized at 122° C. for 20 minutes. After the sterilization, the mixture was cooled down to room temperature. 27 g of m-Cresol was added and the resultant mixture was mixed for one hour. PDGF was added to the sterilized gel using aseptic technique. The resultant gel was then stirred for one hour. The gel had a viscosity of 8200 cps measured at 37° C.

EXAMPLE 4

Carboxymethylcellulose Gels

Carboxymethylcellulose (CMC or NaCMC) gels were prepared according to the present invention. Pharmaceutical grade sodium carboxymethylcellulose (7H3SFPH) was used for this preparation. To a 350 L Turbo Emulsifier mixing vessel was added 247.4 kg of purified water. With the internal homogenizer at the maximum setting (1400 rpm), the following ingredients were added to the mixing vessel: 405 g methylparaben and 45 g propylparaben. The mixture was homogenized for five minutes and then stirred at 16 rpm while the temperature was raised to 60° C. Once the temperature reached 60° C., the solution was stirred for 1 hour. The solution was cooled to 30° C. The following ingredients were then added to this solution: 2020 g sodium chloride, 392 g sodium acetate trihydrate, 1250 g L-lysine hydrochloride, 16.25 g acetic acid and 225 g m-cresol. The resultant mixture was stirred for 15 minutes. This solution was transferred to a 600 L holding tank and 6000 g sodium carboxymethylcellulose was added to the hopper of a Flashblend homogenizer. The liquid was pumped back into the Turbo Emulsifier through the Flashblend homogenizer and the CMC was added to the liquid buffer solution.

The gel thus formed was stirred for 2 hours. A solution of 26.05 g rhPDGF-B in 2631 g water was added to the gel, followed by 100 g of water rinse. The gel was then mixed for 2 hours. The mixing vessel was evacuated and the vacuum broken with nitrogen gas.

The gel was then filled into 15 g tubes. A final viscosity of 75812 cps, measured at 37° C., was achieved.

EXAMPLE 5

Polyacrylic Acid Gels

Polyacrylic acid gels (Carbopol) were prepared according to the present invention. Preferred grades of polyacrylic acid are those referred to as Carbopol 934 P and 940 at concentrations of 0.02–1.5%. Higher concentrations of polyacrylic acid lower the release rate of the EGF. Viscosities of polyacrylic acids are generally stable between pH 6–10, preferably in the pH range 6.5–7.5

The following ingredients were combined in a 4 liter beaker: 6.3 g methylparaben, 0.7 g propylparaben and 177.5 g mannitol in 3500 ml water. This solution was mixed with a paddle type mixer until the solids dissolved. Polyacrylic acid (17.5 g, Carbopol 940, BF Goodrich) was sieved through a 40 mesh screen into the solution while it was mixed at 1,000 rpm. This dispersed and swelled the polyacrylic acid particles. The solution was neutralized to pH 7.0 by the addition of 7.6 grams solid NaOH in 10% solution. A 900 g portion of this gel was removed from the batch and autoclaved to provide a sterile gel. The remainder of the procedure was performed in a class 100 area. A stock solution of EGF at 1.18 miligrams/ml (12 ml) was filtered through a 0.22 micrometer filter into a sterile tube and the filter was washed with a 5 ml aliquot of water into the same tube. The contents of the tube were added to the gel by syringe. The gel was mixed thoroughly with a paddle type mixer to uniformly disperse the EGF. The gel was placed in an autoclaved pressure vessel. Nitrogen was used to force the gel to flow out of the pressure vessel into 10 ml syringes via a sterile piece of tubing. Samples were tested for activity and shown to contain 15.6 micrograms of EGF/ml. The samples were free from microorganisms in a 10 g sample. The viscosity of the gels prepared ranged from about 490,000 to about 520,000 cps. This gel formulation was used in a pig and guinea pig partial thickness skin excision model and the gel showed an enhanced rate and quality of wound healing in these animals.

EXAMPLE 6

Pluronic Gel Formulations

Polyoxyethylene-polyoxypropylene block copolymers (Pluronics) have great potential for use in topical drug delivery systems, since they exhibit reverse thermal gelation behavior and they have good drug release characteristics as well as low toxicity. Low molecular weight Pluronic polyols do not form gels at any concentration in water. Pluronic F-68 forms a gel at a minimum concentration of 50–60% at room temperature. Pluronic F-68 forms a gel at 40% at room temperature and Pluronic F-108 forms a gel at 30% concentration. Pluronic F-127 forms a gel at only 20% concentration in water at 25° C. Pluronic gels of F-68, F-88, F-108 and F-127 may be used for controlled delivery of EGF for burns and other donor site dosage forms. The gel should be isotonic and it is preferred that the pH be in the range 6–8, and more preferably 6.5–7.5.

An interesting property of the Pluronic gels is their ability to gel as a function of temperature and polymer concentration. Gels are formed as the Pluronic solution is warmed. Thus, the gel is a low viscosity aqueous solution at room temperature, but when it contacts the human body and is warmed by body temperature the viscosity increases and the solution gels. EGF may be combined with the Pluronic in the liquid state and applied to the wound. At this point, gelation would occur which would effectively reduce the rate of EGF released to the wound. This permits prolonged contact time between EGF and the epithelium of the wound. The gel could be applied as a liquid or in conjunction with a dressing (soaked in the liquid) to give mechanical support. Advantages of using Pluronic gels include the availability of filtration methods for sterilization of these gels and the wound would be in prolonged contact with the EGF.

A Pluronic F-127 gel containing EGF was prepared by mixing the following: 1.8 g sodium phosphate monohydrate, 5.48 g disodium phosphate heptahydrate and 40.9 g mannitol were combined in 1,000 ml of distilled water. The pH was adjusted to 7.0 and the solution was cooled to 4° C. Pluronic F-127 (200 g) (BASF) was added to the cooled solution gradually while mixing with a paddle type mixer. The solution was mixed for about 30 minutes and then placed at 4° C. overnight. EGF in an aqueous solution may be added to the solution before the gel is made or may be mixed after dissolving the Pluronic F-127 in solution. To obtain an EGF concentration of 100 micrograms/ml, 1.812 ml of an EGF solution (1.38 mg/ml) was added to 23.188 g of 20% Pluronic F-127 gel. The solution is very liquid like. The viscosity of the solution increased as it was warmed to 35° C., as can be seen in Table 1.

TABLE 1

| Temperature °C. | Viscosity (cps, 0.5 rpm) |
|---|---|
| 0–16 | Not detectable |
| 18 | 4,000 |
| 19 | 250,000 |
| 21 | 500,000 |
| 28 | 655,000 |
| 30 | 685,000 |
| 37 | 650,000 |

Additional Pluronic formulations were prepared which had viscosities of 1,000,000 to 12,000,000. The release kinetics of a formulation (11.5×106 cps) was tested and it was noted that 85% of the EGF was released from the formulation within one hour.

EXAMPLE 7

HPMC Gel Formulations

Several HPMC gels were prepared. The gels were made from very low molecular weight to high molecular weight HPMC. Preferably the molecular weight range is from 80,000–240,000. With very low molecular weight polymers (Methocel E15LV), as much as 10–20% HPMC is required to form a gel. For very high molecular weight polymers (Methocel K100M), gels can be made from a 1–3% solution. Gels were made with different grades and different concentrations to study the release kinetics. The pH was adjusted to 7.2 for each gel. The rate of EGF release was proportional to the viscosity of the soluble gel.

In a 1,500 ml beaker were placed 0.83 g sodium phosphate monohydrate, 7.24 g disodium phosphate heptahydrate, 6.22 g NaCl and 500 ml sterile water for irrigation. The mixture was stirred magnetically to dissolve the solids and the pH was adjusted to 7.2. The solution was heated to 80° C. while stirring and 30.0 g of HPMC (Methocel K100M; Dow) was added through a 40 mesh sieve. It was removed from the heat and stirred for 10 more minutes. The remaining water 500 g was added as ice. Stirring was performed by hand as the mixture became more viscous. It was allowed to cool to room temperature and then cooled to 4° C. overnight. A 130 g portion was removed and mixed with 13.4 ml of a 1.12 mg/ml sterile solution of EGF with a paddle mixer to obtain an EGF concentration of 104 micrograms/ml.

The gels prepared had viscosities that ranged from 54,000 to 950,000 cps at room temperature. The release of the EGF from the various HPMC gel formulations prepared is set forth in Table 2.

TABLE 2

| Sample | Brookfield Viscosity (CPS) 25° C. | Brookfield Viscosity (CPS) 37° C. | Release of EGF |
|---|---|---|---|
| 2085-91-1 E4M 4% | $112 \times 10^3$ | $102 \times 10^3$ | 75% in 5 hours |
| 2085-92-2 E4M 5% | $274 \times 10^3$ | $300 \times 10^3$ | 75% in 5 hours |
| 2085-92-2 E4M 6% | $652 \times 10^3$ | $946 \times 10^3$ | 50% in 5 hours |
| 2085-91-2 F4M 4% | $112 \times 10^3$ | $286 \times 10^3$ | 75% in 5 hours |
| 2085-93 K15M 3% | $102 \times 10^3$ | $70 \times 10^3$ | 75% in 5 hours |
| 2085-91-3 K4M 4% | $92 \times 10^3$ | $54 \times 10^3$ | 75% in 5 hours |

EXAMPLE 8

Hyaluronic Acid Gel Formulations

Hyaluronic acid (HA) is one of the mucopolysaccharides having a straight chain structure consisting of the repetition of a disaccharide unit of N-acetylglucosamine and glucuronic acid. HA is found in nature, in microorganisms and in the skin and connective tissue of humans and other animals. Molecular weights of HA are within the range of 50,000–8,000,000 depending on source, methods of preparation and method of determination. Highly viscous solutions of HA have lubricating properties and an excellent moisturizing effect. It is found in the synovial fluid of joints, vitreous body of the eyeball, umbilical cord, skin, blood vessels and cartilage. It works remarkably well as a lubricant and shock absorbing agent and this is probably due to its water retaining ability and its affinity for linking it to certain specific proteins. It is considered to be a very safe molecule for use internally in the human body. Thus, it may be used in internal wound healing such as healing of joints or in the anterior chamber of the eye. A 1% solution of sodium hyaluronate (molecular weight 4,000,000; MedChem) was formulated with EGF to obtain a concentration of 100 micrograms/ml. The viscosity of the 1% HA solution was 44,000 cps. An HA/EGF formulation prepared according to the present invention has been demonstrated to stimulate reendothelialization in the anterior chamber of the eye.

EXAMPLE 9

Kinetics of Release of EGF from Dosage Forms

The effectiveness of each dosage form to sustain the release of EGF in an in vitro diffusion cell system was evaluated and values for $T_{25}$ and $T_{50}$ were determined. EGF is released as a result of both the diffusion of the EGF from the gel and the dissolution of the gel matrix. Taking these two processes as the likely mechanisms by which EGF will be bioavailable in vivo, HPMC gels sustain the release of EGF with the highest values, with $T_{25}$ and $T_{50}$ values of 1.2 and 5.9, respectively. Results indicated that the molecular structure of the polymer was more important than the concentration of the polymer in prolonging T values. Gels that were made in salt free media (distilled water) and studied under standing conditions yielded low T values. This may be a result of a combination of faster dissolution and lower viscosity of salt-free gels. Therefore, it is preferred that the gels of the present invention not be salt-free. It is envisioned that the T values for the gels of the present invention may be increased by modifying the polymer such as by introduction of hydrophobic or hydrophilic side chains, ion pair groups, metal ions, cross-linking agents, affinity groups for EGF to control the release of EGF from the resulting product form.

Table 3 summarizes the kinetic data of the release of EGF from dosage forms. Referring to the Table, the different letters following HPMC refer to the percent substitution in the polymer. For example, K=2208 or 22% methylated and 8% hydroxy-propyl substituted; F=2906; and E=2910. The numerical value following the letter (i.e., the number 100 following the K) refers to the viscosity of a 2% solution in water in thousands cps. AQ refers to gels made in salt-free solution. All other gels were made in phosphate buffered saline (PBS) at a pH of approximately 7.0. T values are in hours.

TABLE 3

Summary of Kinetic Data of the Release of EGF from Dosage Forms

| Polymer | | Viscosity cps | $T_{25}$ | $t_{50}$ |
|---|---|---|---|---|
| HPMC K100M | 1% | — | 0.0854 | 1.000 |
| (mw 240,000) | 2% | $287 \times 10^3$ | 0.4687 | 1.9172 |
| | 3.5% | $116 \times 10^6$ | 1.2270 | 5.8528 |
| | 4.0% | — | 0.8536 | 4.1386 |
| | 5.0% | $3.07 \times 10^6$ | 0.8807 | 3.5808 |
| HPMC K-15M | 3% | $122 \times 10^3$ | 0.857 | 2.0635 |
| (mw 120,000) | 4 AQ % | $331 \times 10^3$ | 0.2727 | 1.6900 |
| HPMC K-4M | 4% | $96 \times 10^3$ | 1.0476 | 2.6349 |
| (mw 86,000) | | | | |
| HPMC F-4M | 4% | $122 \times 10^3$ | 0.7619 | 1.8730 |
| (mw 86,000) | | | | |
| HPMC E-4M | 4% | $128 \times 10^3$ | 1.0159 | 2..2657 |
| (mw 86,000) | 5% | $312 \times 10^3$ | 0.8615 | 1.8462 |
| HPMC E-4M | 5 AQ % | $240 \times 10^3$ | 0.3211 | 1.6044 |
| (mw 86,000) | 6 AQ % | $680 \times 10^3$ | 0.6944 | 3.0040 |
| Carbopol 934P | 0.5% | $494 \times 10^3$ | 0.2727 | 0.7300 |
| (mw $3 \times 10^6$) | | | | |
| Pluronic F-127 | 20% | $1.1 \times 10^6$ | 0.1936 | 0.3548 |
| (mw 12,000) | | | | |

EXAMPLE 10

Polyacrylamide Gel Formulations

Polyacrylamide/EGF gel formulations were prepared using the polyacrylamides Cyanamer N-300 and Cyanamer N-300 LMW (both commercially prepared by American Cyanamid). The Cyanamer N-300 had a molecular weight of about 5–6 million and the Cyanamer N-300 LMW had a molecular weight of about 13 million.

Polyacrylamide gels of the following compositions were prepared by adding the polyacrylamide polymer to the premixed salt solutions. These gels were then used for testing the release of EGF.

TABLE 4

| Composition | % Concentration by weight | |
|---|---|---|
| | 2085-140A | 2085-140B |
| Cyanamer N-300 | 4.0 | — |
| Cyanamer N-300 LMW | — | 4.0 |
| Sodium chloride | 0.049 | 0.049 |
| Potassium chloride | 0.075 | 0.075 |
| Calcium chloride | 0.048 | 0.048 |
| Magnesium chloride | 0.080 | 0.080 |
| Sodium acetate | 0.890 | 0.890 |
| Sodium citrate dehydrate | 0.170 | 0.170 |
| Sterile water | 94.688 | 94.688 |
| Viscosity, cps. | $552 \times 10^3$ | $132 \times 10^3$ |

To 1.809 grams of polyacrylamide gel of Cyanamer N-300 (2085-140A), 72.4 microliters of a mixture of $^{125}$I-EGF and EGF were added and mixed in two 3 milliliter syringes. 300–400 milligrams of this gel was placed in the donor side of a Franz diffusion cell. At predetermined time intervals, 50 microliter aliquots of the receiving buffer was counted on a gamma counter. The receiving buffer consisted of 3.5 milliliters PBS, pH 7.2 containing 0.4% BSA (bovine serum albumin) and 0.02% sodium azide. Similarly, to 1.11 grams of polyacrylamide gel of Cyanamer N-300 LMW (2085-140B), 44.5 microliters of a mixture of $^{125}$I-EGF and EGF were added, and the release of EGF was examined.

Another polyacrylamide gel (2085-138C) was prepared having the following formulation.

TABLE 5

| Composition | 2085-138C |
|---|---|
| Cyanamer N-300 | 7.0 g |
| Thimerosal | 0.2 g |
| Sterile water | 192.8 g |
| viscosity | $258 \times 10^3$ |
| pH | 7.54 |

The 2085-138C gel was used to prepare a gel containing EGF at 10 micrograms/ml. Five grams of the 2085-138C gel was weighed into an 8 ml serum vial and 50 micrograms of 1 mg/ml EGF (protein assay 1.41 mg/ml) was added.

EGF was coated onto a wound dressing and favorable release characteristics were obtained. The wound dressing was a gel film made of polyacrylamide/agar (Geliperm, Geistlich-Pharma; Wolhusen, Switzerland.) The dressing was coated with EGF by soaking the dressing with an aqueous solution of EGF. About 70% of the EGF was released from the dressing in about 24 hours.

Stabilized PDGF Cellulose Polymer Gel Formulation

Carboxymethylcellulose (CMC) gels were prepared according to the present invention. The CMC used in these studies was pharmaeutical grade sodium carboxymethylcellulose (Aqualon Co., Wilmington, Del.) at a 2.4% concentration and a molecular weight range of about 900,000–2,000,000 daltons. The CMC gels were formulated with rhPDGF-BB (Chiron Corporation, Emeryville, Calif.). It has been found that the stability of a PDGF cellulose polymer gel formulation can be greatly increased by including in the formulation a charged chemical species, such as a charged amino acid or a metal ion. As used herein, "stability" refers to a prevention of the loss of mitogenic activity of the PDGF in the gel or an increase in the amount of PDGF protein that is released from the gel. As such, the present invention provides PDGF gel formulations that are useful for treating wounds.

The formulation was tested for in vivo wound healing efficacy in a guinea pig partial thickness skin excision model.

In the guinea pig partial thickness skin excision wound healing model, two partial thickness wounds per guinea pig (4–8 animals per group) were made using a dermatome. The 3×1 cm wounds (typically 0.4–0.8 mm deep) were treated once daily for the first 5 days (days 0–4) with 0.3 ml gel and covered by a sterile absorptive pad. The pads were covered by occlusive dressings and overwrapped with protective bandages at each treatment. The wounds were harvested for histologic evaluation on day 7. The average thickness of the granulation tissue bed was measured by projecting the Gomori's trichrome-stained histology slides onto a computerized digitizing planimeter at 50× magnification. The thickness was obtained by tracing the area of a standard length of granulation tissue in the wound bed and dividing by the length. Three histologic sections of each wound were measured, and the measurements from the two wounds per guinea pig were averaged to give a single value for the animal.

In this model PDGF at concentrations of 10–300 µg/g in the CMC formulation consistently induced a 2–3 (or greater) fold increase in the thickness of the granulation tissue bed of the wounds. Granulation tissue is the newly formed connective tissue and vessels that is a major component of wound healing. Granulation tissue acts to physically fill in the wound defect. Additionally, granulation tissue provides the rich blood supply which the epidermis needs in order to grow over the wound surface. Thus, granulation tissue is an essential component of healing wounds.

The tables show 1) the efficacy of PDGF in the CMC gel, 2) the absence of an effect of lysine on PDGF's efficacy in fresh batches (Table 6), 3) the retention of efficacy for 30 months (stored at 2–8 degrees C.) of the lysine-stabilized formulation (Table 7), and 4) the retention of efficacy of PDGF in a sterile unpreserved CMC (with lysine) formulation (Table 8).

TABLE 6

Effect ot PDGF and Lysine on Granulation Tissue Thickness in Guinea Pig Partial Thickness Wounds

| Treatment | Granulation Tissue Thickness (mm) Mean ± S.E.M. | N (Animals) |
|---|---|---|
| Original CMC | 63.3 ± 15.9 | 7 |
| PDGF(30 µg/g) in CMC | 161.9 ± 25.4* | 7 |
| CMC + 0.1% lysine | 64.4 ± 8.9 | 7 |
| PDGF (30 µg/g) in CMC + 0.1% lysine | 16.26 ± 23.5* | 8 |
| CMC + 0.5% lysine | 59.9 ± 5.6 | 8 |
| PDGF (30 µg/g) in CMC + 0.5% lysine | 144.6 ± 21.8* | 7 |

*Significantly different from its vehicle control (p < 0.05)

The data show that recombinant human platelet-derived growth factor-BB in CMC gel is efficacious in increasing the amount of granulation tissue in experimental guinea pig wounds (here by a factor of 2.5 fold). The data also show that up to 0.5% lysine does not affect the efficacy of PDGF in the CMC formulation.

TABLE 7

Effect of Aged PDGF in Lysine-stabilized CMC on Granulation Tissue Thickness in Guinea Pig Partial Thickness Wounds*

| Treatment | Granulation Tissue Thickness (mm) Mean ± S.E.M. | N (Animals) |
|---|---|---|
| CMC* | 81.4 ± 15.5 | 6 |
| PDGF (30 µg/g) in CMC 30 month batch | 311.3 ± 32.4** | 6 |
| PDGF (30 µg/g) in CMC fresh batch | 217.3 ± 22.3** | 6 |

*All formulations contained 0.5% lysine.
**Different from vehicle control (p < 0.05)

These data show that the formulation containing 0.5% lysine maintained its efficacy in promoting granulation tissue formation in experimental wounds for at least 30 months.

TABLE 8

Effect of PDGF in a Sterile Unpreserved CMC Formulation on Granulation Tissue Thickness in Guinea Pig Partial Thickness Wounds*

| Treatment | Granulation Tissue Thickness (mm) Mean ± S.E.M. | N (Animals) |
|---|---|---|
| Sterile CMC** unpreserved | 150.1 ± 48.5 | 4 |
| PDGF (100 µg/g) in sterile CMC unpreserved | 652.6 ± 58.6*** | 4 |
| PDGF (100 µg/g) in sterile CMC preserved | 635.1 ± 73.5*** | 4 |
| PDGF (100 µg/g) in non-sterile CMC preserved | 752.2 ± 79.5*** | 4 |

*This model was conducted in a different laboratory using substantially deeper wounds than in the lysine study, thus the vehicle control baseline granulation tissue thickness measurements are higher.
**All formulations contained 0.5% lysine.
***Different from vehicle control (p < 0.05)

These data show that the sterile unpreserved PDGF/CMC (with 0.5% lysine) has efficacy in promoting the formation of granulation tissue in wounds.

The mechanism by which a charged chemical species can stabilize a PDGF/cellulose polymer formulation is not known. Without wishing to be bound by theory, the stabilization effect may occur from a competition by the charged species with the PDGF lysines for the reducing end groups of the cellulose polymer and/or by possibly decreasing the charge interactions between the free carboxyl groups of the cellulose polymer and the PDGF lysines. Charge interactions between PDGF and cellulose polymers, such as CMC, have been demonstrated in our labs. Charged chemical species capable of competing with positive and negative charges can reduce the charge interactions between PDGF and a cellulose polymer, thereby increasing PDGF stability. Positively charged counterions were tested for their ability to enhance recovery of PDGF from a CMC gel.

Addressing the question of PDGF-CMC stability first requires an understanding of how PDGF may lose activity in the presence of CMC. One possible mechanism for the loss of such activity is the adsorption and entrapment of PDGF in CMC. The nature of this adsorption involves the entrapment of the highly positively charged PDGF B homodimer (containing 22 arginine residues and 14 lysine residues) with the negatively charged CMC matrix which contains a large number of free carboxyl groups. Our studies of PDGF in CMC have shown a loss of mitogenic activity and a decrease in protein released when little or no counterions are present to offset this charge interaction.

The increase of PDGF stability in a CMC gel can be accomplished by minimizing the charge interactions between PDGF or by minimizing interaction with the reducing ends of the CMC by adding competing positively or negatively charged counterions. In one experiment, lysine (0.5% w/w) increased PDGF stability in CMC by more than 50%. Any compound capable of reducing or competing with the PDGF-CMC charge interaction or interaction with the reducing ends of CMC may improve PDGF stability in CMC. It is understood that the charged chemical species in the present formulations are initially added to the formulation in salt form. The salt then dissociates in the aqueous environment of the gel to provide the respective charged chemical species. As used herein the phrase "charged chemical species" includes pharmaceutically acceptable versions of the following: salts, such as zinc and magnesium chloride; buffers, such as mono/diethanolamine, fumaic acid, malic acid, potassium citrate and sodium gluconate; amino acids, such as lysine, arginine, histidine, aspartic acid, glutamic acid, alanine, methionine, proline, serine, asparagine, cystein;; aminoguanidine and protamine; ionic surfactants, such as oleic acid and oleth 5; and synthetic poly-cationic or ionic polymers, such as polyamino acids. As used herein, the phrase "pharmaceutically acceptable" means that the material so described may be used for treatment in or on humans or other mammals without causing ill effects, such as toxicity, blistering or whitening of mucosa or skin tissue.

In addition to the experiments set forth below, 0.5% aminoguanidine also improved the recovery of PDGF from a cellulose polymer gel. Aminoguanidine is a better competitor than lysine in preventing the non-enzymatic glycosylation of proteins because of its strong nucleophilic nature.

The present invention is intended to encompass formulations that contain cellulose polymers, or any other polymers with potential reducing ends, and a pharmaceutically acceptable nucleophilic counterion, such as lysine or aminoguanidine.

Experiment #1

Samples used were rhPDGF-B mixed with CMC placebo, 0.5 hours old and rhPDGF-BB in CMC, 60 days old at 4° C. Table 9 shows the effect of $Zn^{++}$ concentration on PDGF recovery. The 0 day old sample showed a higher percent recovery than the 60 day old sample with the same $Zn^{++}$ concentration. These data suggest that PDGF ionically binds to CMC and that, with time, this binding possibly crosslinks the CMC so that more $Zn^{++}$ is required for PDGF release.

PDGF recovery was measured by reverse phase HPLC on a C4 300 angstrom macrosphere column using a 10–70% acetonitrile gradient with 0.1% TFA.

TABLE 9

| | % rhPDGF Recovery | |
|---|---|---|
| Molarity, Zn | 0 Day Old | 60 Day Old |
| 0.075 | 84 | 71 |
| 0.15 | 88 | 81 |
| 0.3 | 97 | 90 |

Table 10 shows the effect of other charged compounds on the recovery of PDGF from a CMC gel. 0.5 grams of a 60 day old sample of PDGF was dissolved in 10 ml of $H_2O$ with 0.01% BSA (which was used as the control) and the listed compounds were added to each sample.

TABLE 10

| Sample Recovery | % PDGF |
|---|---|
| A Control | 50 |
| B 0.2M NaCl (mono +) | 42 |
| C 0.2M $ZnCl_2$ (di ++) | 64 |
| D 0.2M $CaCl_2$ (di ++) | 63 |
| E 0.2M $MgCl_2$ (di ++) | 69 |
| F 0.5% lysine (+, zwitterion) | 64 |
| G 0.5% glycine (zwitterion) | 50 |

These data suggest that the more positively charged Zn, Ca, Mg and lysine can minimize the PDGF-CMC charge interaction. They also suggest that PDGF may become entangled or entrapped within the CMC matrices.

Experiment #2

This set of experiments was designed to test various amino acids on PDGF recovery in CMC. The samples used were 100 µg PDGF per gram CMC, pH 6.0, buffer 0.13 m NaCl, plus 0.5% of an amino acid. The samples were incubated at 46° C. for two days in polypropylene tubes and then analyzed as before on RP-HPLC.

Data from a comparative evaluation on the effect of nonpolar and polar amino acids on the recovery of PDGF in CMC are set forth in Table 11. The formulations which contained the more highly charged amino acids (lysine, aspartic acid and glutamic acid) provided the greatest recovery of PDGF. All amino acids are zwitterions at pH near 7.0. Hence, they will all give enhanced recoveries depending on the charge of the R-group. The more charged the R group is (e.g., lysine), the better the stabilizing effect.

TABLE 11

| Effect of Various Classes of Amino Acids on PDGF | |
|---|---|
| RECOVERY IN CMC SAMPLES | % Recovery Compared to Zero Time Control |
| Control, zero time | 100.0 |
| CMC + no AA | 37.3 |
| NONPOLAR SIDE CHAINS | |
| Glycine | 43.4 |
| Alanine | 37.5 |
| Methionine | 40.8 |
| Proline | 40.2 |
| UNCHARGED POLAR SIDE CHAINS | |
| Serine | 48.7 |
| Asparagine | 39.9 |

TABLE 11-continued

| Effect of Various Classes of Amino Acids on PDGF | |
|---|---|
| RECOVERY IN CMC SAMPLES | % Recovery Compared to Zero Time Control |
| Tyrosine | 45.5 |
| Cysteine | 42.0 |
| CHARGED POLAR SIDE CHAINS | |
| Lysine pk9 | 64.0 |
| Aspartic Acid pk4 | 70.4 |
| Glutamic Acid pk4 | 58.2 |

The effect of various other charged compounds on PDGF recovery in CMC was also evaluated and the data are set forth in Table 12. In these experiments 100 µg PDGF in 1 gram of CMC was used. The data show that as the NaCl concentration is increased from 0M to 1.13M, the % recovery of PDGF increased from 32% to 96%. $Mg^{++}$ at 0.1M gave 94.8% recovery.

TABLE 12

| Effect of Various Charged Compounds on PDGF Recovery in CMC | |
|---|---|
| Samples | % Recovery Based on Zero Time |
| Control, zero time | 100.0 |
| CMC + 0.0M NaCl (water only) | 32.1 |
| CMC + 0.0M NaCl (buffer only) | 27.6 |
| CMC + 0.13M NaCl | 65.9 |
| CMC + 0.33M NaCl | 82.8 |
| CMC + 0.63M NaCl | 90.7 |
| CMC + 0.94M NaCl | 93.8 |
| CMC + 1.13M NaCl | 96.8 |
| CMC + 0.0M NaCl + MgCl2 0.1M | 94.8 |
| CMC + 0.13M NaCl + Gly 0.5% | 76.7 |
| CMC + 0.13M NaCl + Lys 0.5% | 85.5 |

Experiment #3

One month mitogenic stability data of rhPDGF (30 µg/g) with lysine and without lysine are set forth in Table 13. The data were determined using the fibroblast thymidine uptake method and are represented in terms of the content of rhPDGF measured. The data show that the presence of lysine in the formulation increases the mitogenic activity of the formulation.

TABLE 13

| | rhPDGF µg/g | |
|---|---|---|
| | Without Lys (n = 10) | With Lys (n = 4) |
| 25° C. | 16.8 +/− 4 | 31.2 +/− 7 |
| 30° C. | 10.4 +/− 2 | 27.0 +/− 0.5 | rhPDGF-BB Cellulose Polymer Formulations

Cellulose polymer gel formulations containing rhPDGF-BB may be formulated according to generally accepted formulation techniques. In general, preparation of an intimate mixture of the required ingredients is all that is required. By "intimate mixture", is meant that the ingredients of the composition are mixed substantially uniformly so that none of those ingredients are localized.

The compositions of the present invention contain a "wound healing effective amount" of PDGF, which is an amount sufficient to increase the rate of healing of a wound. As is well known in the medicinal arts, effective amounts of medicinal agents vary with the particular agent employed, the condition being treated and the subject being treated. Consequently, effective amounts of treating agents may not be defined for each agent. Thus, a wound healing effective amount of PDGF is that amount which in a composition of the present invention provides a sufficient amount of PDGF in or on the body of the treated subject for the desired period of time, and is typically less than that amount usually used. One gram of typical compositions of this invention may contain from about 1.0 µg to about 1000 µg PDGF. Preferably, a composition of this invention may contain from about 1 µg to about 300 µg PDGF, per gram of formulation.

Additional ingredients such as buffers, preservatives, tonicity adjusting agents, anti-oxidants, other polymers (used, e.g. to adjust viscosity or as extenders), and excipients may be used in the compositions of the present invention. Specific illustrative examples of such other materials include phosphate, citrate or borate buffers; thimerosal, sorbic acid, methylparaben or propylparaben, m-cresol and chlorobutanol preservatives; sodium chloride and/or sugars to adjust the tonicity; polymers such as polyvinyl alcohol, poly (acrylic acid) and polyvinyl pyrrolidone; and excipients such as mannitol, lactose, sucrose, ethylene diamine tetraacetic acid, and the like.

A general cellulose polymer gel formulation containing rhPDGF-BB is set forth in Table 14. The viscosity of such formulation is in the range 1000–150,000 cps at room temperatuare.

TABLE 14

| Ingredient | Concentration Range |
| --- | --- |
| rhPDGF-BB | 1.0–1,000 mg per gram of gel |
| cellulose polymer | 1.5–3.0% (w/w) |
| charged chemical species | 0.1–3.0% (w/w) |
| preservative(s) | 0.15–0.25% (w/w) |

Specific formulations containing rhPDGF-B are set forth in Tables 15, 16 and 17.

TABLE 15

| Ingredient | Quantity | % (w/w) |
| --- | --- | --- |
| Purified Water | 100 g | 96.02 |
| | Quantity g/100 g Purified Water | |
| Methylparaben | 0.1620 g | 0.16 |
| Propylparaben | 0.0180 g | 0.02 |
| Sodium Acetate Trihydrate | 0.1570 g | 0.15 |
| Lysine Hydrochloride | 0.5000 g | 0.48 |
| Sodium Chloride | 0.8086 g | 0.78 |
| m-Cresol | 0.0900 g | 0.09 |
| Glacial Acetic Acid | 0.0065 g | 0.01 |
| Sodium Carboxymethylcellulose | 2.4000 g | 2.30 |
| | Quantity g/100 g Gel | |
| rhPDGF-B (Bulk Stock sol'n) | 0.0036 g | |

TABLE 16

| Ingredient | Amount/250 kg batch | Amount/g gel |
| --- | --- | --- |
| Acetic acid | 15.6 g | 0.06 mg |
| Sodium chloride | 1946.3 g | 7.70 mg |
| Sodium acetate trihydrate | 377.9 g | 1.51 mg |
| L-Lysine monohydrochloride | 1203.5 g | 4.81 mg |
| Water for injection | 240700.0 g* | 962.80 mg |
| Sodium CMC | 5776.8 g | 23.11 mg |
| rhPDGF-BB (bulk drug) | 25.0 g | 0.10 mg |

*Total WFI includes 2500 g in the liquid bulk drug substance

TABLE 17

| Ingredient | g/100 g of gel |
| --- | --- |
| rhPDGF-BB | 0.01 |
| Sodium carboxymethylcellulose | 2.40 |
| Sodium chloride | 0.8086 |
| Sodium acetate trihydrate | 0.1570 |
| Glacial acetic acid | 0.0065 |
| Methylparaben | 0.1620 |
| Propylparaben | 0.0180 |
| m-Cresol | 0.0900 |
| L-Lysine hydrochloride | 0.5000 |
| Water for injection | 100.00 |

(ingredients in g/100 g of water for injection except rhPDGF-B which is in g/100 g of gel)

The invention has been described herein with reference to certain preferred embodiments and examples. It is readily apparent that obvious variations may appear to those skilled in the art. In particular, one skilled in the art may be able to vary the molecular weights and percent concentrations of the various polymers to achieve the desired viscosities. Also, one skilled in the art may be able to substitute different polymers or growth factors for those recited herein. Since obvious variations will appear to those skilled in the art, the invention is not to be considered limited thereto but only by the claims which follow.

What is claimed is:

1. A pharmaceutical composition comprising:
   a) an effective epidermal, ophthalmic or cutaneous wound healing amount of platelet derived growth factor (PDGF);
   b) a pharmaceutically acceptable cellulose polymer; and
   c) a pharmaceutically acceptable charged chemical species other than PDGF selected from the group consisting of lysine, arginine, histidine, protamine, alanine, methionine, proline, serine, asparagine, cysteine, aminoguanidine, zinc and magnesium, wherein the composition is an aqueous gel having a viscosity in the range of about 1000 to 500,000 cps at room temperature.

2. The composition of claim 1, wherein the PDGF is the PDGF-B homodimer.

3. The composition of claim 1, wherein the cellulose polymer is selected from the group consisting of carboxymethylcellulose, hydroxypropylmethyl cellulose and methyl cellulose.

4. The composition of claim 1, wherein the PDGF concentration is within the range of about 1.0 µ/gram to about 1,000 µ/gram.

5. The composition of claim 1, wherein the cellulose polymer concentration is about 1.5% (w/w) to about 3.0% (w/w) and the polymer has a molecular weight of about 450,000 to about 4,000,000.

6. The composition of claim 1, wherein the concentration of the charged species is within the range of about 0.1% (w/w) to about 3.0% (w/w).

7. The composition of claim 1, wherein the viscosity is in the range of 50,000–150,000.

8. The composition of claim 1, which additionally comprises a preservative.

9. The composition of claim 8, wherein the preservative is selected from one or more of the group consisting of methylparaben, propylparaben and m-cresol.

10. A method for healing a cutaneous, ophthalmic or epithelial wound in a patient, comprising contacting the wound with a composition of claim 1.

11. A pharmaceutical composition comprising:

a) an effective epithelial, ophthalmic or cutaneous wound healing amount of human PDGF B homodimer;

b) carboxymethylcellulose (CMC); and c) lysine, wherein the composition is an aqueous gel having a viscosity in the range of about 1000 to 500,000 cps at room temperature.

12. The composition of claim 11, wherein the cellulose polymer concentration is about 1.5% (w/w) to about 3.0% (w/w) and the polymer has a molecular weight of about 450,000 to about 4,000,000.

13. The composition of claim, 11 wherein the lysine concentration is within the range of about 0.1% (w/w) to about 3.0% (w/w).

14. The composition of claim 11, wherein the viscosity is in the range from 1000 to 150,000.

15. The composition of claim 11, which additionally comprises a preservative.

16. The composition of claim 15 wherein the preservative is selected from one or more of the group consisting of methylparaben, propylparaben and m-cresol.

17. A method for healing a cutaneous, ophthalmic or epithelial wound in a patient, comprising contacting the wound with a composition of claim 11.

18. A pharmaceutical composition, comprising:

a) an effective epithelial, ophthalmic or cutaneous wound healing amount of platelet derived growth factor (PDGF);

b) a pharmaceutically acceptable cellulose polymer at a concentration in the range of about 1.5% (w/w) to about 3.0% (w/w) and having a molecular weight in the range of about 450,000 to about 4,000,000; and c) a pharmaceutically acceptable positively charged chemical species other than PDGF selected from the group consisting of positively charged amino acids, positively charged polyamino acids and positively charged metal ions at a concentration in the range of about 0.1% (w/w) to about 3.0% (w/w), wherein the composition is an aqueous gel having a viscosity in the range of about 1000 to 500,000 cps at room temperature.

19. The composition of claim 18, wherein the viscosity is in the range from 1000 to 150,000.

20. The composition of claim 18, which additionally comprises a preservative.

21. The composition of claim 20 wherein the preservative is selected from one or more of the group consisting of methylparaben, propylparaben and m-cresol.

22. The formulation of claim 18, wherein the charged chemical species is selected from the group consisting of lysine, arginine, histidine, protamine, alanine, methionine, proline, serine, asparagine, cysteine, aminoguanidine, zinc and magnesium.

23. A pharmaceutical composition of claim 15, comprising (g/100 g of gel) 0.01 g of rhPDGF-B; 2.40 g of sodium carboxymethylcellulose; 0.81 g of sodium chloride; 0.157 g of sodium acetate trihydrate; 0.0065 g of glacial acetic acid; 0.162 g of methylparaben; 0.018 g of propylparaben; 0.09 g of m-cresol; 0.5 g of l-lysine hydrochloride; and 100 g water for injection, having a viscosity in the range from about 20,000 to about 200,000 cps at 37° C.

24. A pharmaceutical composition of claim 11, comprising (mg/g of gel) 0.1 g of rhPDGF-B; 23.103 g of sodium carboxymethylcellulose; 7.784 g of sodium chloride; 1.511 g of sodium acetate trihydrate; 0.0624 g of glacial acetic acid; 4.813 g of l-lysine hydrochloride; and 962.63 g of water, having a viscosity in the range from about 1000 to about 15,000 cps at 37° C.

25. A method for healing cutaneous, ophthalmic or epidermal wound in a patient, comprising contacting the wound with the composition of claim 22.

26. A method for healing a cutaneous, ophthalmic or epidermal wound in a patient, comprising contacting the wound with the composition of claim 23.

27. A pharmaceutical composition, comprising:

a) an effective epidermal, ophthalmic or cutaneous wound healing amount of platelet derived growth factor (PDGF);

b) a pharmaceutically acceptable cellulose polymer; and c) a pharmaceutically acceptable charged chemical species other than PDGF.

28. The composition of claim 27 wherein the cellulose polymer concentration is about 1.5 to about 3.0% by weight and the polymer has a molecular weight of about 500,000 to about 800,000.

29. The composition of claim 27 wherein the charged species is present in an amount sufficient to increase the amount of PDGF that can be released from the composition.

30. The composition of claim 27 wherein the charged chemical species is present in an amount sufficient to reduce the interaction between PDGF and the cellulose polymers.

31. A pharmaceutical composition, comprising:

a) an effective epidermal, ophthalmic or cutaneous wound healing amount of human PDGF B—B homodimer;

b) carboxymethylcellulose (CMC); and c) lysine.

32. The composition of claim 31 wherein the cellulose polymer concentration is about 1.5 to about 3.0% by weight and the polymer has a molecular weight of about 500,000 to about 800,000.

33. The composition of claim 31 wherein the lysine concentration is within the range of about 0.1% to about 3.0% by weight.

34. The composition of claim 31 wherein the composition is in the form of a gel having a viscosity within the range of about 50,000 cps to about 150,000 cps at room temperature.

35. The composition of claim 31 wherein the lysine is present in an amount sufficient to increase the amount of PDGF that is released from the composition.

36. The composition of claim 31 wherein the lysine is present in an amount sufficient to reduce the interaction between PDGF and the CMC.

* * * * *